(12) United States Patent
Rosenbloom

(10) Patent No.: US 7,914,823 B2
(45) Date of Patent: *Mar. 29, 2011

(54) METHOD AND COMPOSITION FOR THE TOPICAL TREATMENT OF DIABETIC NEUROPATHY

(75) Inventor: Richard Allen Rosenbloom, Elkins Park, PA (US)

(73) Assignee: Prophase Labs, Inc., Doylestown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/369,025

(22) Filed: Feb. 19, 2003

(65) Prior Publication Data

US 2003/0138504 A1    Jul. 24, 2003

Related U.S. Application Data

(62) Division of application No. 09/740,811, filed on Dec. 21, 2000, now Pat. No. 6,555,573.

(51) Int. Cl.
*A61K 35/78* (2006.01)

(52) U.S. Cl. .......................................... 424/725; 514/167

(58) Field of Classification Search .................. 514/456, 514/458, 474, 725, 733
See application file for complete search history.

(56) References Cited

U.S. PATENT DOCUMENTS

| | | | |
|---|---|---|---|
| 4,147,795 A | 4/1979 | Sarges | |
| 4,210,667 A | 7/1980 | Sarges et al. | |
| 4,232,040 A | 11/1980 | Waterbury | |
| 4,250,097 A * | 2/1981 | Pfister | 549/393 |
| 4,591,600 A | 5/1986 | Creuzet et al. | |
| 4,617,187 A | 10/1986 | Okuyama et al. | |
| 4,627,973 A | 12/1986 | Moran et al. | |
| 4,822,816 A | 4/1989 | Markham | |
| 4,997,649 A | 3/1991 | Papaconstantin et al. | |
| 5,011,840 A | 4/1991 | Sarges | |
| 5,043,323 A | 8/1991 | Bombardelli et al. | |
| 5,070,085 A | 12/1991 | Markham | |
| 5,122,536 A | 6/1992 | Perricone | |
| 5,194,248 A | 3/1993 | Holick | |
| 5,545,398 A | 8/1996 | Perricone | |
| 5,550,249 A | 8/1996 | Della Valle et al. | |
| 5,561,110 A | 10/1996 | Michaelis et al. | |
| 5,571,441 A | 11/1996 | Andon et al. | |
| 5,574,063 A | 11/1996 | Perricone | |
| 5,595,982 A | 1/1997 | Harless | |
| 5,607,666 A | 3/1997 | Masson et al. | |
| 5,614,224 A | 3/1997 | Womack | |
| 5,626,868 A | 5/1997 | Morancais et al. | |
| 5,626,883 A * | 5/1997 | Paul | 424/605 |
| 5,648,083 A | 7/1997 | Blieszner et al. | |
| 5,660,818 A | 8/1997 | Dubief et al. | |
| 5,665,360 A | 9/1997 | Mann | |
| 5,665,367 A | 9/1997 | Burger et al. | |
| 5,686,082 A | 11/1997 | N'Guyen | |
| 5,686,367 A | 11/1997 | Hayashi | |
| 5,709,868 A | 1/1998 | Perricone | |
| 5,710,177 A | 1/1998 | Sauermann et al. | |
| 5,725,844 A | 3/1998 | Gers-Barlag et al. | |
| 5,770,260 A | 6/1998 | Fukuyama et al. | |
| 5,776,460 A | 7/1998 | Kim et al. | |
| 5,804,168 A | 9/1998 | Murad | |
| 5,824,666 A * | 10/1998 | Deckner et al. | 514/152 |
| 5,840,736 A | 11/1998 | Zelle et al. | |
| 5,866,578 A * | 2/1999 | Mylari et al. | 514/256 |
| 5,872,140 A | 2/1999 | Hesse et al. | |
| 5,876,737 A | 3/1999 | Schonrock et al. | |

(Continued)

FOREIGN PATENT DOCUMENTS

CA     2280093     6/1998

(Continued)

OTHER PUBLICATIONS

Fukuoka, M. et al., "Novel pharmacological activity of a vitamin (novel pharmacological action of vitamin D)", Medscape Medline abstract, Nippon Yakurigaku Zasshi Oct. 1997, 110 Suppl. 1:39P-43P.*

(Continued)

*Primary Examiner* — Ardin Marschel
*Assistant Examiner* — Bong-Sook Baek
(74) *Attorney, Agent, or Firm* — Knoble, Yoshida & Dunleavy, LLC

(57) ABSTRACT

A method and composition for the treatment of diabetic neuropathy is disclosed. The composition comprises a cold compounded mixture of a compound that promotes synthesis of nerve growth factor, an aldose reductase inhibitor and an antioxidant formulated in a pharmaceutically acceptable carrier. It has been found that this combination of active agents provides significant, effective relief of the symptoms of diabetic neuropathy, as well as at least partial recovery of lost neurological function in some cases. In view of the consensus in the art that effective combinations of various active agents have not been demonstrated to be effective for the treatment of diabetic neuropathy, the present invention provides a surprising and unexpected effect. In addition, the topical compositions of the present invention, when used in effective amounts to treat diabetic neuropathy, do not exhibit the severe side effects of many prior art compositions proposed for treatment of this ailment.

In a second aspect, a method for the topical administration of a composition in accordance with the present invention for the treatment of diabetic neuropathy is disclosed. In the method, an effective amount of the composition of the invention is topically administered to the areas of the body that have been adversely affected by the diabetic neuropathy on a regular basis over a period of time sufficient to provide the beneficial effects of relief from the symptoms and at least some recovery of the damaged nerve tissues.

12 Claims, No Drawings

U.S. PATENT DOCUMENTS

| | | | |
|---|---|---|---|
| 5,883,086 A | 3/1999 | Craft | |
| 5,922,335 A * | 7/1999 | Ptchelintsev | 424/401 |
| 5,928,670 A * | 7/1999 | Kador et al. | 424/558 |
| 5,948,443 A | 9/1999 | Riley et al. | |
| 5,952,391 A | 9/1999 | Gers-Barlag et al. | |
| 5,958,379 A | 9/1999 | Regenold et al. | |
| 5,972,359 A | 10/1999 | Sine et al. | |
| 5,972,923 A | 10/1999 | Simpkins et al. | |
| 5,972,999 A | 10/1999 | Murad | |
| 5,976,568 A | 11/1999 | Riley | |
| 5,976,579 A | 11/1999 | McLean | |
| 5,977,184 A * | 11/1999 | Birdsall et al. | 514/685 |
| 5,981,594 A | 11/1999 | Okamoto et al. | |
| 5,998,394 A | 12/1999 | Voorhees et al. | |
| 6,048,886 A | 4/2000 | Neigut | |
| 6,051,602 A | 4/2000 | Bissett | |
| 6,054,128 A | 4/2000 | Wakat | |
| 6,069,168 A * | 5/2000 | Horrobin et al. | 514/474 |
| 6,103,709 A | 8/2000 | Norman et al. | |
| 6,103,756 A * | 8/2000 | Gorsek | 514/458 |
| 6,121,243 A | 9/2000 | Lanzendorfer et al. | |
| 6,162,801 A | 12/2000 | Kita | |
| 6,296,861 B1 | 10/2001 | Perricone | |
| 6,299,896 B1 | 10/2001 | Cooper et al. | |
| 6,391,344 B2 * | 5/2002 | Kosaka et al. | 424/725 |
| 6,423,747 B1 | 7/2002 | Lanzendorfer et al. | |
| 6,444,221 B1 | 9/2002 | Shapiro | |
| 6,451,837 B1 | 9/2002 | Baskys | |
| 6,455,057 B1 | 9/2002 | Barrett et al. | |
| 6,555,573 B2 * | 4/2003 | Rosenbloom | 514/456 |
| 6,562,794 B1 | 5/2003 | Lanzendorfer et al. | |
| 6,576,660 B1 | 6/2003 | Liao et al. | |
| 6,592,896 B2 | 7/2003 | Rosenbloom | |
| 6,596,313 B2 | 7/2003 | Rosenbloom | |
| 6,596,761 B2 | 7/2003 | Lanzendorfer et al. | |
| 7,083,813 B2 * | 8/2006 | Rosenbloom | 424/725 |
| 7,410,659 B2 | 8/2008 | Rosenbloom | |
| 2001/0031744 A1* | 10/2001 | Kosbab | 514/54 |

FOREIGN PATENT DOCUMENTS

| | | | |
|---|---|---|---|
| EP | 1283037 A1 | | 2/2003 |
| JP | 60-120812 | | 6/1985 |
| JP | 60120812 | * | 6/1985 |
| JP | 01096106 | | 4/1989 |
| JP | 3232851 | | 10/1991 |
| JP | 07324037 A | | 12/1995 |
| JP | 200080044 | | 3/2000 |
| WO | 96262607 A1 | | 8/1996 |
| WO | WO 97/18817 | | 5/1997 |
| WO | 9831381 A1 | | 7/1998 |
| WO | 9841113 A2 | | 9/1998 |
| WO | 0011968 A1 | | 3/2000 |
| WO | 0035848 A1 | | 6/2000 |
| WO | 0059522 A1 | | 10/2000 |

OTHER PUBLICATIONS

Riaz S. et al., "A vitamin D3 derivative (CB1093) induces nerve growth factor and prevents neurotrophic deficits in streptozotocin-diabetic rats", Medscape Medline Abstract, Diabetologia Nov. 1999, 42(11): 1308-1313.*

Okada, Y. et al., "Search for naturally occuring substances to prevent the complications of diabetes II . Inhibitory effect of coumarin and flavonoid derivatives on bovine lens aldose reductase and rabbit platelet aggregation.", Medscape Medline Abstract, Chem. Pharm Bull (Tokyo) Aug. 1995, 43(8):1385-1387.*

Hardman, J. G. Editor-in-Chief of Goodman & Gilman's The Pharmacological Basis of Therapeutics, 9th Edition, pp. 1493-1498, 1996.*

Holick, M.F., "Noncalcemic Actions of 1,25-Dihydroxyvitamin D3 and Clinical Applications," Bone, vol. 3, No. 2, pp. 107S-111S (1995).*

Riaz, S., et al, "A Vitamin D3 Derivative (CB1093) Induces Nerve Growth Factor and Prevents Neurotrophic Deficits in Streptozotocin-Diabetic Rats," Diabetologia, vol. 42, No. 11, pp. 1308-1313 (Abstract)(1999).*

Bravenboer, B., et al., "Potential Use of Glutathione for the Prevention and Treatment of Diabetic Neuropathy in the Streptozotocin-Induced Diabetic Rat," Diabetologia, vol. 35, pp. 813-817 (1992).*

Riaz et al. (Diabetologia, 42:1308-1313, 1999).*

Nuraliev et al, The Efficacy Of Quercetin In Alloxan Diabetes, Eksperimental 'naia I klinicheskaia farmakologiia (Jan.-Feb. 1992) 55 (1) 42-4.

Riaz, S. et al., "A Vitamin D3 Derivative (CB1093) Induces Nerve Growth Factor and Prevents Neurotrophic Deficits in Streptozotocin-Diabetic Rats," Diabetologia, 1999, pp. 1308-1313, vol. 42, No. 11. Chemical Abstract No. 131:332572.

Masami Fukuoka et al., "Novel Pharmacalogical Action of Vitamin D," Folia Pharmacology Japan, 1997, pp. 39-43, vol. 110, Supplement No. 1.

Kengo Maeda et al., "Diabetic Neuropathy: Clinical and Experimental Progress in its Pathogenesis and Treatment," Nippon Rinshou, 1999, pp. 88-93, vol. 57, No. 3.

Hotta, N. "Diagnosis and Treatment of Diabetic Neuropathies," Nippon Naika Gakkai Zasshi, 1999, pp. 145-151, vol. 88, No. 11.

Igakunoayumi, 1999, pp. 597-601, vol. 188, No. 5.

Gendaiiryou, 1998, pp. 144-150, vol. 30, No. 10.

Iryou Journal, 1997, pp. 175-180, vol. 33, No. 10.

Baird, Stuart A. et al., "Anhydrosis in the Diabetic Foot: A Comparison of Two Urea Creams—Research," The Diabetic Foot, 2003.

Fukuoka, Masami et al., "Tacalcitol, An Active Vitamin D3, Induces Nerve Growth Factor Production in Human Epidermal Keratinocytes," Skin Pharmacology and Applied Skin Physiology, 2001, 226-233, vol. 14.

Schoemaker, J.H., "Pharmacological Treatment of Diabetic Peripheral Neuropathy: Challenges and Possibilities," British Journal of Clinical Practice, 1994, pp. 91-96, vol. 48, No. 2.

Varma, S.D. et al., "Flavonoids as Inhibitors of Lens Aldose Reductase," Science, 1995, pp. 1215-1216, vol. 188.

Lavinia Androne et al., "In Vivo Effect of Lipoic Acid on Lipid Peroxidation in Patients with Diabetic Neuropathy," In Vivo, 14: 327-330 (2000).

Prem S. Chaudhry et al., "Inhibition o Human Lens Aldose Reductase by Flavonoids, Sulindac and Indomethacin," Biochemical Pharmacology, vol. 32, No. 13, 1995-1998 (1983).

Office Action dated Aug. 7, 2007; Canadian Patent Application No. 2,431,079; "Method and Composition for the Treatment of Diabetic Neuropathy".

Van Dam, et al. "Oxidative Stress and Antioxidant Treatment in Diabetic Neuropathy", Neuroscience Research Communications, vol. 21, May 1997, pp. 41-48.

Fukuoka, et al., "Tacalcitol, an Active Vitamin D3, Induces Nerve Growth Factor Production in Human Epidermal Keratinocytes", Skin Pharmacol Appl Skin Physiol, 2001, 14, pp. 226-233.

Roche Vitamins for Cosmetics, pp. 1 to 5, Sep. 4, 1985.

Natural Medicine Online, "Quercetin: A Review of Clinical Applications" by L. Stephen Coles M.D., Ph.D., pp. 1 to 5, (Jul. 2000).

Cosmetic Dermatology, Dec. 1991, "Topical Vitamin C May Help Protect Skin from UV Damage" by William F. Dial, pp. 34 and 35.

"Ultraviolet Irradiation Injury and Repair" by Bernard Idson, Ph.D., Jan. 1992, pp. 78 to 81.

"Role of Nitric Oxide in Pain" by Jai Pal Singh, Doo Hyam Lee, Asavari Wagle and David Lodge, 2000 Academic Press.

"The Neuronal NO synthase inhibitor 7-nitro-indazole facilitates the antinociception elicited by the electrical stimulation of the secondary somatosensory cortex in the rat" by Ryotaro Kuroda, Atsufumi Kawabata, Naoyuki Kawao, Wakana Umeda, Hiroko Yoshimura, 2000 Academic Press.

"Over-the Counter Drug is Treatment for Alzheimer's" by Terri Mitchell and Amber Needham, LE Magazine, Nov. 2000, p. 1 to 9.

"Ascorbate 6-palmitate protects human erythrocytes from oxidative damage", Jan. 1999, PubMed.

"Analgesic activity of certain flavone derivatives: a structure-activity study", Jan. 1993, PubMed.

Perricone N et al., The hydroxyl free radical reactions of ascorbyl palmitate as measured in various in vitro models, *Biochem Biophys Res Commun* Sep. 7, 1999;262(3):661-5.

Liu ZQ, et al., "Making vitamin C lipophilic enhances its protective effect against free radical induced peroxidation of low density lipoprotein", *Chem Phys Lipids*, Sep. 1998;95(1):49-57.

Fukuoka M, et al., "Novel pharmacological activity of a vitamin (novel pharmacological action of vitamin D)", *Nippon Yakurigaku Zasshi*, Oct. 1997;110 Suppl 1:39P-43P.

Riaz S, et al., "A vitamin D(3) derivative (CB1093) induces nerve growth factor and presents neurotrophic deficits in streptozotocin-diabetic rats", *Diabetologia*. Nov. 1999;42(11):1308-13.

Vincent TE, et al., "Inhibition of aldose reductase in human erythrocytes by vitamin C", *Diabetes Res Clin Pract* Jan. 1999;43(1):1-8.

Cunningham JJ, et al., "Vitamin C: an aldose reductase inhibitor that normalizes erythrocyte sorbitol in insulin-dependent diabetes mellitus", *J Am Coll Nutr*, Aug. 1994;13(4):344-50.

Cunningham JJ, "The glucose/insulin system and vitamin C: implications in insulin-dependent diabetes mellitus", *J Am Coll Nutr* Apr. 1998;17(2):105-8.

Crabbe MJ, et al., "Aldose reductase: a window to the treatment of diabetic complications?", *Prog Retin Eye Res* Jul. 1998;17(3):313-83.

Fujita T, et al., "Inhibitory effects of perillosides A and C, and related monoterpene glucosides on aldose reductase and their structure-activity relationships", *Chem Pharm Bull* (Tokyo) Jun. 1995;43(6):920-6.

Guillausseau PJ, Preventive treatment of diabetic micorangiopathy: blocking the pathogenic mechanisms, *Diabete Metab*, 1994;20(2 Pt 2):219-28.

McAuliffe AV et al., "Administration of ascorbic acid and an aldose reductase inhibitor (tolrestat) in diabetes: effect on urinary albumin excretion" *Nephron* Nov. 1998;80(3):277-84.

Eaton RP, et al., "A commentary on 10 years of aldose reductase inhibition for limited joint mobility in diabetes", *J Diabetes Complications* Jan.-Feb. 1998;12(1):34-8.

Rastelli G, et al. "Structural bases for the inhibition of aldose reductase by phenolic compounds", *Bioorg Med Chem*, May 2000;8(5):1151-8.

Costantino L,et al., "Diabetes complications and their potential prevention: aldose reductase inhibition and other approaches" *Med Res Rev*, Jan. 1999;19(1):3-23.

Hosotani H, et al., "Effects of topical aldose reductase inhibitor CT-112 on corneal sensitivity of diabetic rats" *Curr Eye Res* Oct. 1996;15(10):1005-7.

Medscape Medline Abstract, "Inhibition of aldose reductase by dihydroflavonols in *Engelhardtia chrysolepis* and effects on other enzymes" by, Ohmi I, Masuda H, Tamura Y, Mizutani K, Tanaka O and Chou WH, Jun. 1996.

Haraguchi H, et al., "Topical Aldose reductase inhibitor for correcting corneal endothelial changes in diabetic patients" *Experientia* Jun. 15, 1996;52(6):564-7.

Benstead TJ, et al., "Nerve microvessel changes in diabetes are prevented by aldose reductase inhibition", *Can J Neurol Sci* Aug. 1995;22(3):192-7.

Okada Y, et al., "Search for naturally occurring substances to prevent the complications of diabetes. II. Inhibitory effect of coumarin and flavonoid derivatives on bovine lens aldose reductase and rabbit platelet aggregation" *Chem Pharm Bull* (Tokyo) Aug. 1995;43(8):1385-7.

Costantino L, et al., "1-Benzopyran-4-one antioxidants as aldose reductase inhibitors", *J Med Chem* Jun. 3, 1999;42(11):1881-93.

Nishimura-Yabe C, "Aldose reductase in the polyol pathway: a potential target for the therapeutic intervention of diabetic complications" *Nippon Yakurigaku Zasshi* Mar. 1998;111(3):137-45.

Tomlinson DR, et al., "Aldose reductase inhibitors and their potential for the treatment of diabetic complications" *Trends Pharmacol Sci* Aug. 1994;15(8):293-7.

Airey M, et al., "Aldose reductase inhibitors for the prevention and treatment of diabetic peripheral neuropathy", *Cochrane Database Syst Rev* 2000;(2):CD002182.

Maxwell SR, et al., "Antioxidant status in patients with uncomplicated insulin-dependent and non-insulin-dependent diabetes mellitus", *Eur J Clin Invest* Jun. 1997;27(6):484-90.

Himmerich S., et al., "Effect of Vitamins E and C on Nitric Oxide Production in Oxidized Low Density Lipoprotein Treated Human Aortic Endothelial Cells", *Academic Press*; 2000, internet download at http://www.academicpress.com/www/journal/niox/9204.html.

Asahi K, et al.,"Nitric Oxide Inhibits the Formation of Advanced Glycation End Products", *Kidney Int* Oct. 2000;58(4):1780-7.

McCarty MF, "Nitric oxide deficiency, leukocyte activation and resultant ischemia are crucial to the pathogenesis of diabetic retinopathy/neuropathy—preventive potential of antioxidants, essential fatty acids, chromium, ginkgolides, and pentoxifylline" *Med Hypotheses* May 1998;50(5):435-49.

Boulton AJ,et al., "Guidelines for diagnosis and outpatient management of diabetic peripheral neuropathy", *Diabetes Metab* Nov. 1998;24 Suppl 3:55-65.

Tutuncu NB et al., "Reversal of defective nerve conduction with vitamin E supplementation in type 2 diabetes: a preliminary study", *Diabetes Care*, Nov. 1998;21(11):1915-8.

van Dam PS, et al., "Diabetic peripheral neuropathy: international guidelines for prevention, diagnosis, and treatment (comment)", *Ned Tijdschr Genneeskd* Feb. 26, 2000;144(9):418-21.

Zangaro GA et al., "Diabetic neuropathy: pathophysiology and prevention of foot ulcers" *Clin Nurse Spec* Mar. 1999;13(2):57-65; quiz 66-8.

Boulton AJ, et al., "Diabetic Neuropathy", *Med Clin North Am*, Jul. 1998;82(4):909-29.

Feldman EL, et al., "Pathogenesis of diabetic neuropathy" *Clin Neurosci*, 1997;4(6):365-70.

Qian M, et al., "Glycochelates and the etiology of diabetic peripheral neuropathy" *Free Radic Biol Med* Feb. 15, 2000;28(4):652-6.

Galer BS,et al., "Painful diabetic polyneuropathy: epidemiology, pain description, and quality of life", *Diabetes Res Clin Pract* Feb. 2000;47(2):123-8.

Kaneto H, et al., "Beneficial effects of antioxidants in diabetes: possible protection of pancreatic beta-cells against glucose toxicity" *Diabetes* Dec. 1999;48(12)2398-406.

DiSilvestro R., "Zinc Deficiency-Diabetes Link Explored", internet download May 31, 2000 at http://wwwl.rf.ohio-state.edu/pubrpt/mh/zinc.htm.

Chusid, R., "Vitamins and Diabetes", internet download Sep. 25, 2000 at http://ourworld.com.compuserve.com/homepages/rchusid.vdm.htm.

"Alternative Therapies for Diabetes" by National Diabetes Information Clearinghouse, May 1999.

Salonen JT et al., "Increased risk of non-insulin dependent diabetes mellitus at low plasma vitamin E concentrations: a four year follow up study in men" *BMJ* Oct. 28, 1995;311(7013):1124-7.

Fox GN et al., "Chromium picolinate supplementation for diabetes mellitus" *Fam Pract* Jan. 1998;46(1):83-6.

Nutrition Dynamics Inc., "Glyco Control.", (Feb. 1998).

Diabetic Polyneuropathy, "Pathophysiology", vol. 1, 1999, Medscape, Inc.

Diabetic Polyneuropathy, "Future Therapies", vol. 1, 1999, Medscape, Inc.

Diabetic Poyneuropathy, "Neurologic Examination", vol. 1, 1999, Medscape, Inc.

Diabetic Polyneuropathy, "Symptom History", vol. 1, 1999, Medscape, Inc.

Van Acker et al., "Structural Aspects of Antioxidant Activity of Flavonoids", *Free Radic Biol Med* 1996;20(3):331-42.

Ohguro N, et al., "Topical Aldose reductase inhibitor for correcting corneal endothelial changes in diabetic patients" *Br J Opthalmol*. Dec. 1995;79(12):1074-7 Abstract.

Tiukavkima, et al., "Dihydorquercetin—a new antixodant and biologically active food additive", Vopr Pitan 1997;(6):12-5 Abstract.

Plumb, et al., "Antioxidant properties of flavonal glycosides from tea", *Redox Rep* 1999;4(1-2):13-6 Abstract.

Duke, et al., "Biological Activities of Curcuminoids", Phytochemical and Ethnobotanical Database, (Jan. 3, 2002).

Robak, et al., "Bioactivity of flavonoids", *Pol J Pharmacol* Nov.-Dec. 1996;48(6):555-64 Abstract.

Bursel, et al., "Can protein kinase C inhibition and vitamin E prevent the development of diabetic vascularcomplications?", *Diabetes Res Clin Pract* Sep. 1999; 45(2-3):169-82 Abstract.

Freedman, et al., "Select flavonoids and whole juice from purple grapes ihibit platelet function and enhance nitric oxide release", *Circulation* Jun. 12, 2001;103(23):2792-8 Abstract.

Lin, et al., "Recent studies on the biofunctions and biotransformations of curcumin", *Biofctors* 2000;13(1-4):153-8 Abstract.

Duarte, et al., "Vasodilator effects of quercetin in isolated rat vascular smooth muscle", *Eur J Pharmacol* Aug. 1993 239:1-7 Abstract.

Giugliano, et al., "Oxidative stress and diabetic vascular complications", *Diabetes Care* Mar. 1996;19(3):257-67 Abstract.

Okada, Y, et al (cont) Chem. Pharm Bull (Tokyo) Aug. 1995, 43(8): 1385-1387. Abstract.

Sports Medicine Articles (online), Sep. 1, 2000 (retrieved on Jan. 10, 2002) Retreived from the Internet http://www.rehabnet.com/Sports/Actinic%20Dermatitis.htm, p. 1-2.

* cited by examiner

METHOD AND COMPOSITION FOR THE TOPICAL TREATMENT OF DIABETIC NEUROPATHY

This is a divisional of U.S. application Ser. No. 09/740,811 filed on Dec. 21, 2000, now U.S. Pat. No. 6,555,573.

BACKGROUND OF THE INVENTION

1. Field of the Invention

The present invention relates to a method and composition for the topical treatment of diabetic neuropathy. More particularly, the present invention relates to a topical composition including a combination of ingredients that provide a surprising degree of effective relief from the symptoms of diabetic neuropathy and to a method for administering the topical composition to treat diabetic neuropathy.

2. Description of the Prior Art

Diabetes mellitus is a common disease that is usually classified into insulin-dependent and non-insulin dependent types. Both types may be managed by diet, in combination with insulin in the first type and a variety of drugs in the second type. However, while the changes in blood glucose associated with diabetes can usually be managed reasonably satisfactorily by conscientious patients and doctors, this does not prevent long term damage to many tissues as a result of the disease. This damage may take many forms but the major types are damage to the eyes (retinopathy), nerves (neuropathy), kidneys (nephropathy) and cardiovascular system.

There are many approaches to reducing or preventing these forms of damage, which are collectively known as the long-term complications of diabetes. One approach is based on damage that results from over-production of the glucose metabolite, sorbitol, in the cells of the body. Glucose can be converted to sorbitol by the enzyme aldose reductase. High levels of sorbitol may be among the causes of diabetic complications such as diabetic neuropathy. As a result, a number of pharmaceutical companies have been developing aldose reductase inhibitors for the purpose of reducing diabetic neuropathy.

It has been established that a wide variety of flavanoids are effective inhibitors of aldose reductase, including such flavanoids as quercetin, quercetrin and myrecetrin. However, U.S. Pat. No. 4,232,040 discloses that despite the fact that these flavanoids have been shown in in vitro studies to be among the most potent flavanoids for aldose reductase inhibition, a need exists for aldose reductase inhibitors that can be more effectively used and in lower doses than the prior art compounds, including these flavanoids.

In fact, numerous patents are devoted to goal of developing improved aldose reductase inhibitors. Among these patents are U.S. Pat. Nos. 6,069,168; 5,011,840; 4,210,667; 4,147,795; 5,866,578; and 5,561,110. Numerous other patents also exist which relate to aldose reductase inhibitors.

Another approach to the treatment of neuropathy is disclosed in U.S. Pat. No. 5,840,736 (Zelle et al.). In this method, pharmaceutical compositions for stimulating the growth of neurites in nerve cells comprising a neurotrophic amount of a compound and a nerve growth factor. These compositions may be administered in a number of ways including orally and topically.

Still another approach to the treatment of neuropathy is disclosed in U.S. Pat. No. 5,550,249 (Della Ville et al.). In this approach, compositions suitable for treatment of vitamin H deficiencies are administered for the treatment of neuropathy. This patent relates to biotin salts with alkanolamines. The compositions may be administered orally, parenterally or topically.

U.S. Pat. No. 5,665,360 (Mann) relates to the treatment of peripheral neuropathies associated with diabetes mellitus by periodic topical application of a composition containing capsicum oleoresin as the active ingredient. When applied to the skin of the affected area, pain and burning associated with the neuropathy are said to be reduced. However, capsicum oleoresin has been shown to kill nerve endings in some cases and thus this composition suffers from this disadvantage.

U.S. Pat. No. 5,981,594 (Okamoto et al.) relates to a method of treatment of diabetic neuropathy using combined administration of a formulation including as an active ingredient, a prostaglandin I derivative with an anti-diabetic agent in order to improve nerve conduction velocities. Suitable anti-diabetic agents include oral hypoglycemic agents and insulin.

The Okamoto patent also contains a detailed discussion of the various types of neuropathy that may be associated with diabetes. According to this patent, nerve conduction velocity (NCV) is the most widely used method of objectively evaluating the severity of diabetic neuropathy. This patent also mentions that current methods of treating diabetic neuropathy such as dietetic therapy, administration of insulin, administration of aldose reductase inhibitors or aminoguaninidine to improve abnormal glucose metabolism, administration of troglitazone or agents for the improvement of blood flow have been tested but found to be insufficient when a single drug was used. Also, according to this patent, methods of treatment by combined use of different therapeutic agents which have different functions had yet to be established. The patent concludes that combined drug therapies for diabetic neuropathy, aiming at recovering once reduced nerve conduction velocity, have not yet been confirmed.

There remains a need in the art for an effective treatment for diabetic neuropathy that does not suffer from the disadvantage that it causes severe side effects, as do many aldose reductase inhibitors, for example.

Accordingly, it is the primary object of the present invention to provide a topical composition that is effective for the treatment of diabetic neuropathy.

It is another object of the present invention to provide a topical composition for the treatment of diabetic neuropathy which does not cause serve side effects in the patients treated with the composition.

These and other objects of the present invention will be apparent from the summary and detailed descriptions of the invention which follow.

SUMMARY OF THE INVENTION

In a first aspect, the present invention relates to a topical composition for the treatment of diabetic neuropathy. The composition comprises a cold compounded mixture of a compound that promotes synthesis of nerve growth factor, an aldose reductase inhibitor and an antioxidant formulated in a pharmaceutically acceptable carrier. It has been found that this combination of active agents provides significant, effective relief of the symptoms of diabetic neuropathy, as well as at least partial recovery of lost neurological function in some cases. In view of the consensus in the art that effective combinations of various active agents have not been demonstrated to be effective for the treatment of diabetic neuropathy, the present invention provides a surprising and unexpected effect. In addition, the topical compositions of the present invention, when used in effective amounts to treat diabetic neuropathy, do not exhibit the severe side effects of many prior art compositions proposed for treatment of this ailment.

In a second aspect, the present invention relates to a method for the topical administration of a composition in accordance with the present invention for the treatment of diabetic neuropathy. In the method, an effective amount of the composition of the invention is topically administered to the areas of the body that have been adversely affected by the diabetic neuropathy on a regular basis over a period of time sufficient to provide the beneficial effects of relief from the symptoms and at least some recovery of the damaged nerve tissues.

In a third aspect, the present invention relates to a pharmaceutically acceptable carrier for topical compositions that provides excellent dispersions and/or solutions of active ingredients and good penetration through the skin to the areas to be treated. The carrier for topical compositions may also include one or more materials that provide beneficial properties to the skin since many sufferers from diabetic neuropathy develop skin problems such as ulcers, lesions or cell damage.

DETAILED DESCRIPTION OF THE PREFERRED EMBODIMENTS

In a first aspect, the present invention relates to a topical composition for the treatment of diabetic neuropathy. The composition includes a compound that promotes synthesis of nerve growth factor, an aldose reductase inhibitor and an antioxidant formulated in a pharmaceutically acceptable carrier for a topical composition.

The compound that promotes synthesis of nerve growth factor may be selected from suitable compounds that have been shown to have this activity. Suitable compounds that promote synthesis of nerve growth factor are those that do not induce significant, adverse side effects when topically applied to a patient in amounts that promote synthesis of nerve growth factor, and which do not react with one or more of the ingredients of the topical composition resulting in a substantial loss of activity of one or more active ingredients. Preferred compounds for promoting synthesis of nerve growth factor are those that occur naturally in the human body and/or materials obtained from plants or animal which may be ingested or topically applied by humans without significant, adverse side effects in the amounts used or derivatives thereof.

Exemplary compounds that promote synthesis of nerve growth factor are vitamin $D_3$, vitamin $D_3$ derivatives such as 1(S), 3(R)-dihydroxy-20(R)-(1-ethoxy-5-ethyl-5-hydroxy-2-heptyn-1-yl)-9, 10-seco-pregna-5(Z), 7(E), 10 (19)-triene. The preferred nerve growth factor used in the topical composition is vitamin $D_3$. Also, pharmaceutically acceptable salts of the compounds that promote synthesis of nerve growth factor may be employed.

The compound that promotes synthesis of nerve growth factor is used in an amount effective to promote the synthesis of nerve growth factor of about 10,000 to about 3 million IU. per kg of the composition. More preferably, the compound that promotes synthesis of nerve growth factor is employed in an amount of about 50,000 to about 2 million IU per kg of the composition, and most preferably an amount of 100,000 to about 1 million IU is used per kg of the composition.

The preferred compounds that induce synthesis of nerve growth factor may, in addition to this activity, also function to prevent neurotropic deficits. This additional effect of the preferred compounds may also contribute to the overall beneficial effect of the topical composition of the present invention.

In order to formulate the compound that promotes synthesis of nerve growth factor in the topical composition of the present invention, it may be necessary to use a dispersant. Suitable dispersant materials are known to persons skilled in the art. A particularly suitable dispersant for the compounds that promote synthesis of nerve growth factor is corn oil. Corn oil also has the advantage that it is a natural product. The amount of corn oil used is an amount sufficient to disperse the compound that promotes synthesis of nerve growth factor.

The second active ingredient of the topical composition of the present invention is an aldose reductase inhibitor. Numerous suitable aldose reductase inhibitors are known to persons skilled in the art. Again, suitable aldose reductase inhibitors are those that do not induce significant, adverse side effects when topically applied to a patient in an amount effective for aldose reductase inhibition, and which do not react with one or more of the ingredients of the topical composition resulting in a substantial loss of activity of one or more active ingredients of the composition. Preferred aldose reductase inhibitors are those that occur naturally in the human body and/or materials obtained from plants or animal which may be ingested or topically applied by humans without significant, adverse side effects in the amounts used or derivatives thereof.

As mentioned above, numerous aldose reductase inhibitors are known to persons skilled in the art. However, significant adverse side effects are associated with the use of many aldose reductase inhibitors in humans. Thus, it is important to select one or more aldose reductase inhibitors for use in the topical composition of the present invention based on minimizing the risk associated with use of the aldose reductase inhibitor taking into account the amount of that particular inhibitor that must be employed to achieve the desired level of aldose reductase inhibition. Different aldose reductase inhibitors exhibit different levels of inhibition. With this in mind, the preferred aldose reductase inhibitors for use in the topical compositions of the present invention are flavonoids and flavonoid derivatives. Exemplary aldose reductase inhibitors include (−)-epigallocatechin; (−)-epigallocatechin-gallate; 1,2,3,6-tetra-o-gallyol-β-d-glucose; 2'o-acetylacetoside; 3,3',4-tri-o-methyl-ellagic acid; 6,3',4'-trihydroxy-5,7,8-trinethoxyflavone; 6-hydroxy-luteolin; 6-hydroxykaempferol-3,6-dimethyl ether; 7-o-acetyl-8-epiloganic acid; acacetin; acetoside; acetyl trisulfate quercetin; amentoflavone; apiin; astragalin; avicularin; axillarin; baicalein; brazilin; brevifolin carboxylic acid; caryophyllene; chrysin-5,7-dihydroxyflavone; chrysoeriol; chrysosplenol; chrysosplenoside-a; chrysosplenoside-d; cosmosiin; δ-cadinene; dimethylmussaenoside; diacerylcirsimaritin; diosmetin; dosmetin; ellagic acid; ebinin; ethyl brevifolin carboxylate; flavocannibiside; flavosativaside; genistein; gossypetin-8-glucoside; haematoxylin; hispiduloside; hyperin; indole; iridine; isoliquiritigenin; isoliquiritin; isoquercitrin; jionoside; juglanin; kaempferol-3-rhamnoside; kaempferol-3-neohesperidoside; kolaviron; licuraside; linariin; linarin; lonicerin; luteolin; luetolin-7-glucoside; luteolin-7-glucoside; luetolin-7-glucoronide; macrocarpal-a; macrocarpal-b; macrocarpal-d; macrocarpal-g; maniflavone; methy scutellarein; naringenin; naringin; nelumboside; nepetin; nepetrin; nerolidol; oxyayanin-a; pectolinarigenin; pectolinarin; quercetagetin; quercetin; quercimertrin; quercitrin; quercitryl-2" acetate; reynoutrin; rhamnetin; rhoifolin; rutin; scutellarein; sideritoflavone; sophoricoside; sorbarin; spiraeoside; trifolin; vitexin; and wogonin. The most preferred flavonoid and/or flavonoid derivative aldose reductase inhibitors are quercetin, quercetrin, myricetin, kaempferol and myrecetrin since these compounds exhibit a high level of aldose reductase inhibition in combination with a relatively low toxicity. Also, pharmaceutically acceptable salts of these aldose reductase inhibitors may be employed.

The flavonoids and flavonoid derivatives are also preferred since some of these compounds may provide additional beneficial effects in the composition of the present invention. For example, quercetin may act as a chelator for transition metals that some studies have linked to certain symptoms of diabetic neuropathy. Flavonoids may also have some anti-inflammatory activity and/or may help stabilize cell membranes, both of which activities may be beneficial in the treatment of diabetic neuropathy.

The aldose reductase inhibitor is used in an amount of about 2 to about 40 grams per kg of the composition. More preferably, the aldose reductase inhibitor is employed in an amount of about 5 to about 30 grams and most preferably an amount of 8 to about 20 grams per kg of the composition.

Another active ingredient in the composition of the present invention is the antioxidant The antioxidant may be a single compound or a mixture of two or more compounds. Also, the antioxidant may include one or more compounds that provide additional beneficial effects beyond the antioxidant activity, such as aldose reductase inhibition.

Compounds which may be used as antioxidants are those which exhibit antioxidant activity when administered topically without causing any severe adverse side affects when used in an amount effective to provide sufficient antioxidant activity, and which do not react with one or more of the ingredients of the topical composition resulting in a substantial loss of activity of one or more active ingredients. Preferred antioxidants are those that occur naturally in the human body and/or materials obtained from plants or animal which may be ingested or topically applied by humans without significant, adverse side effects in the amounts used or derivatives thereof.

More preferred antioxidants are selected from ascorbyl palmitate, ascorbic acid (vitamin C), vitamin A, vitamin E acetate, α-lipoic acid, especially DL-α-lipoic acid, coenzyme Q10, glutathione, catechin, glangin, rutin, luteolin, morin, fisetin, silymerin, apigenin, gingkolides, hesperitin, cyanidin, citrin and derivatives thereof which exhibit antioxidant activity. Even more preferably, mixtures of two or more antioxidants are employed in the composition of the present invention. Particularly preferred antioxidant mixtures are ascorbyl palmitate with one or both of vitamin A and vitamin E acetate. The antioxidants may also be used in the form of their pharmaceutically acceptable salts and this may be preferred in some cases to increase solubility or dispersability, to reduce adverse side effects, etc.

The antioxidant is used in an amount of about 1 to about 50 grams per kg of the composition. More preferably, the antioxidant is employed in an amount of about 2 to about 30 grams, and most preferably an amount of about 5 to about 20 grams per kg of the composition.

The antioxidants used in the composition of the present invention are preferably selected not only for their antioxidant activity, but also based on other beneficial effects that particular compounds may provide. For example, ascorbyl palmitate not only has antioxidant activity, but also may act as an aldose reductase inhibitor and may help prevent degradation of nitric oxide (NO) and thus is a particularly preferred antioxidant for the present invention. Similarly, vitamin E may also help prevent degradation of nitric oxide and is thus a preferred antioxidant. Vitamin A is a fat-soluble material and thus is preferred for use due to this additional beneficial property. However, due to its solubility characteristics, vitamin A may need to be formulated in a suitable dispersant such as corn oil in much the same manner as vitamin $D_3$ as described above.

Suitable additional beneficial properties for compounds useful in the compositions of the present invention include absorbability when applied topically, aldose reductase inhibition, antioxidant properties, free radical scavenging, transition metal chelation, nitric oxide stabilization, and anti-inflammatory activity, which may have a beneficial effect on the pain of other disorders such as fibromyalgia.

The compositions in accordance with the present invention may provide one or more of the following beneficial effects to a patient when topically applied in effective amounts: relief of pain, burning, tingling, electrical sensations and/or hyperalgesia, increased microcirculation, nitric oxide stabilization, promotes healing of skin ulcers and lesions, protein kinase C inhibition, decreased oxidative stress, anti-inflammation, protection against radiation damage, particularly ultraviolet radiation, blockage of the formation of leukotrienes, stabilization of cell membranes, and promotion of the synthesis of nerve growth factor.

The method of the present invention involves the topical application of a composition of the present invention to areas of the skin in the vicinity of tissue that suffers from diabetic neuropathy. In particular, the present invention is useful on the patients' extremities such as the fingers, toes, hands and feet where diabetic neuropathy is often the most pervasive.

In the method, a suitable amount of the composition of the invention is applied one to six times daily as needed to relieve pain and other symptoms of the diabetic neuropathy. Preferably, the composition is applied two to four times daily, as needed for pain. A sufficient amount should be applied to cover the area afflicted with the diabetic neuropathy with a thin layer of the composition and the composition should be rubbed into the skin until little or no residue remains on the skin. Treatment begins initially to treat acute symptoms but may be continued indefinitely to relieve pain, prevent symptoms of diabetic neuropathy from returning and possibly restore some nerve and/or skin function.

The method of the present invention may provide one or more of the beneficial effects described above for the compositions of the invention. In addition, the method of the present invention may provide some additional beneficial effects due to one or more of the ingredients contained in the pharmaceutically acceptable carrier as described in more detail below.

The pharmaceutically acceptable carrier of the present invention is suitable for use as a carrier for topical compositions wherein the active ingredients are dissolved, dispersed and/or suspended in the composition. The carrier of the present invention contains at least a hydrophilic ointment base, panthenol or a panthenol derivative and a dispersant if needed to disperse one or more insoluble or partially insoluble active ingredients in the carrier.

Suitable hydrophilic ointment bases are known to persons skilled in the art. Exemplary hydrophilic ointment bases suitable for use in the present invention are non-U.S.P. hydrophilic ointment bases such as those made by Fougera, Inc. Sufficient hydrophilic ointment base is employed to act as a carrier for the active ingredients of the composition. Typically the hydrophilic ointment base will make up more than about 80% of the total composition and more preferably about 80-90% of the composition is the hydrophilic ointment base. The hydrophilic ointment base functions as a carrier and enhances penetration into the skin.

The panthenol or panthenol derivatives useful in the present invention include at least D-panthenol, DL-panthenol and mixtures thereof. This component of the carrier has skin moisturizing properties and acts as a quick, deep penetrating component of the carrier that helps deliver the active ingredients through the skin to the area to be treated and imparts a healing effect to damaged tissue. The amount of panthenol or panthenol derivative to be employed is from about 0.25 to about 10 weight percent, more preferably from about 0.5 to about 5 weight percent and most preferably from about 1 to about 2 weight percent, based on the total weight of the composition.

The carrier of the present invention may also include additional ingredients such as other carriers, moisturizers, humectants, emollients dispersants, radiation blocking compounds, particularly UV-blockers, as well as other suitable materials that do not have a significant adverse effect on the activity of the topical composition. Preferred additional ingredients for inclusion in the carrier are sodium acid phosphate moisturizer, witch hazel extract carrier, glycerine humectant, apricot kernal oil emollient, and corn oil dispersant.

Other materials which may optionally be included in the topical compositions of the present invention include inositol, other B-complex vitamins, and anti-inflammatory agents. The composition of the present invention may also be employed to facilitate wound healing, for the treatment of skin cancer and/or one or more symptoms thereof or as a composition for protecting skin from the harmful effects of radiation such as radiation breakdown.

The composition of the present invention is made by cold compounding. This is an important feature of the invention since one or more of the compounds employed in the topical composition are sensitive to heat or other types of energy and thus the activity of the composition may be detrimentally affected as a result of the formulation of the compositions in other manners. Thus, the ingredients of the topical composition the present invention are merely mixed together, without heating using a sufficient amount of the carrier to provide a substantially homogeneous cream or ointment. It may be necessary to dissolve, disperse or suspend one or more of the ingredients prior to cold compounding in order to ensure substantially homogeneous distribution of the active ingredients in the composition.

A preferred composition of the invention can be made using the following ingredients, all based on use of one pound of hydrophilic ointment base. 25-35 cc of a 50% aqueous solution of sodium acid phosphate moisturizing agent, 5-10 cc of D- or DL-panthenol, 5-10 cc of glycerine, 1-3 cc of apricot kernal oil, 3-5 cc of a dispersion of vitamins A and $D_3$ in a corn oil base, 10-20 cc of witch hazel extract, 0.5-2 cc of vitamin E acetate, 2-4 grams of ascorbyl palmitate and 4-8 grams of quercetin powder. Optionally, one or more of the glycerin, witch hazel extract, vitamins A and E and/or the ascorbyl palmitate can be reduced or eliminate from a particular composition, if desirable or larger amounts of one type of component, i.e. antioxidant, can be employed while reducing the amount of another component of the same type or having a similar type of activity.

The invention will now be further illustrated by the following example.

EXAMPLE 1

A topical composition including a mixture of an hydrophilic ointment base, sodium acid phosphate moisturizing agent, a witch hazel extract carrier, glycerine, apricot kernal oil and DL-panthenol as the pharmaceutically acceptable carrier and vitamins A and $D_3$, ascorbyl palmitate, quercetin and vitamin E acetate was prepared by cold compounding. The formulation of the composition is given in Table 1.

The composition was prepared by first placing the hydrophilic ointment base in a stainless steel bowl and mixing briskly until the ointment becomes creamy. Then, the sodium acid phosphate, panthenol, ascorbyl palmitate, glycerine, apricot kernal oil, vitamins A and $D_3$, witch hazel extract, vitamin E acetate and quercetin are added in that order. After each ingredient is added, mixing is continued until all traces of dry ingredients have disappeared and a substantially homogeneous mixture is obtained. The final color should be a consistent yellow and the cream should have the consistency of cake frosting. The mixture is then placed in a sterile container. All containers which contact the composition during mixing must also be sterilized with, for example. zephiran choride or a chlorox solution such as betadine.

This composition was topically administered, under the supervision of a physician, to several patients diagnosed with the most difficult cases of diabetic peripheral neuropathy. The topical composition was applied twice daily in the morning and afternoon, except that patients were permitted to apply the composition up to six times daily, as needed for pain relief over a period of a few days. All of the eight patients treated experienced immediate positive results that lasted up to a day or two after treatment was discontinued. The effects noted by the patients included the relief of burning pain, tingling, healing of damaged skin, and reversal of skin discoloration due to impaired circulation.

TABLE 1

| Ingredient | Amount Employed |
| --- | --- |
| Hydrophilic ointment base | 1 pound |
| 50% aqueous solution of Sodium acid phosphate | 25 cc |
| DL-panthenol | 5 cc |
| Glycerine | 5 cc |
| Apricot kernal oil | 3 cc |
| Witch hazel extract | 12 cc |
| Vitamin E acetate | 1 cc |
| Ascorbyl Palmitate | 2 grams |
| Quercetin powder | 4 grams |

The foregoing detailed description of the invention and examples are not intended to limit the scope of the invention in any way and should not be construed as limiting the scope of the invention. The scope of the invention is to be determined from the claims appended hereto.

What is claimed is:

1. A method for the treatment of diabetic neuropathy which comprises the step of topically applying to the skin of an area afflicted with diabetic neuropathy, an effective amount of a topical composition which comprises:

an amount of a compound that promotes synthesis of nerve growth factor selected from the group consisting of: vitamin $D_3$: 1(S), 3(R)-dihydroxy-20(R)-(1-ethoxy-5-ethyl-5-hydroxy-2-heptyn-1-yl)-9, 10-seco-pregna-5 (Z), 7(E), 10(19)-triene: pharmaceutically acceptable salts thereof and mixtures thereof, which is effective when administered topically in the topical composition to promote synthesis of nerve growth factor;

an amount of quercetin or pharmaceutically acceptable salts thereof, which is effective when administered topically in the topical composition to inhibit aldose reductase;

an effective amount of an antioxidant; and a pharmaceutically acceptable carrier suitable for topical application of the composition to treat diabetic neuropathy.

2. A method as claimed in claim 1, wherein the antioxidant comprises at least one compound selected from the group consisting of: ascorbyl palmitate, ascorbic acid (vitamin C), vitamin A, vitamin E acetate, α-lipoic acid, coenzyme Q10, glutathione, catechin, glangin, rutin, luteolin, morin, fisetin, silymerin, apigenin, gingkolides, hesperitin, cyanidin, citrin, and pharmaceutically acceptable salts thereof.

3. A method as claimed in claim 1, wherein the compound that promotes the synthesis of nerve growth factor is vitamin $D_3$ and the antioxidant is at least one compound selected from the group consisting of vitamin A, vitamin E acetate, and ascorbyl palmitate.

4. A method as claimed in claim 3, wherein the antioxidant comprises vitamin A, vitamin E acetate and ascorbyl palmitate.

5. A method as claimed in claim 3, wherein the antioxidant comprises vitamin E acetate.

6. A method as claimed in claim 1, wherein the amount of the compound that promotes synthesis of nerve growth factor is from 10,000 to 3 million IU per kilogram of the composition, the amount of quercetin or pharmaceutically acceptable salts thereof is from 2-40 grams per kilogram of the composition, and the amount of antioxidant is from 1-50 grams per kilogram of the composition.

7. A method as claimed in claim 2, wherein the amount of the compound that promotes synthesis of nerve growth factor is from 10,000 to 3 million IU per kilogram of the composition, the amount of quercetin or pharmaceutically acceptable salts thereof is from 2-40 grams per kilogram of the composition, and the amount of antioxidant is from 1-50 grams per kilogram of the composition.

8. A method as claimed in claim 7, wherein the compound that promotes synthesis of nerve growth factor is vitamin $D_3$ and the antioxidant is vitamin E acetate.

9. A method as claimed in claim 2, wherein the amount of the compound that promotes synthesis of nerve growth factor is from 50,000 to 2 million IU per kilogram of the composition, the amount of quercetin or pharmaceutically acceptable salts thereof is from 5-30 grams per kilogram of the composition, and the amount of antioxidant is from 2-30 grams per kilogram of the composition.

10. A method as claimed in claim 9, wherein the compound that promotes synthesis of nerve growth factor is vitamin $D_3$ and the antioxidant is vitamin E acetate.

11. A method as claimed in claim 2, wherein the amount of the compound that promotes synthesis of nerve growth factor is from 100,000 to 1 million IU per kilogram of the composition, the amount of quercetin or pharmaceutically acceptable salts thereof is from 8-20 grams per kilogram of the composition, and the amount of antioxidant is from 5-20 grams per kilogram of the composition.

12. A method as claimed in claim 11, wherein the compound that promotes synthesis of nerve growth factor is vitamin $D_3$ and the antioxidant is vitamin E acetate.

* * * * *